(12) United States Patent  (10) Patent No.: US 7,304,582 B2
Kerr, II et al.  (45) Date of Patent: Dec. 4, 2007

(54) REMOTELY MONITORED MEDICAL SYSTEM

(76) Inventors: Robert A. Kerr, II, 446 Catalina Dr., Newport Beach, CA (US) 92663; James D. Fonger, 151 Hampton Crest Trail, Columbia, SC (US) 29209

( * ) Notice: Subject to any disclaimer, the term of this patent is extended or adjusted under 35 U.S.C. 154(b) by 623 days.

(21) Appl. No.: 10/697,684

(22) Filed: Oct. 29, 2003

(65) Prior Publication Data

US 2004/0139048 A1  Jul. 15, 2004

Related U.S. Application Data

(60) Provisional application No. 60/423,206, filed on Oct. 31, 2002.

(51) Int. Cl.
*G05B 23/02* (2006.01)
*G08B 23/00* (2006.01)
*G06F 17/00* (2006.01)

(52) U.S. Cl. .................. 340/573.4; 700/241; 700/242; 340/3.14

(58) Field of Classification Search ............ 340/573.1, 340/573.4, 540, 539.11–539.18, 531, 501–506, 340/539.1, 686.1, 693.5, 3.1, 3.9, 3.3, 3.31, 340/3.71, 5.1–5.33, 5.8–5.85, 825.36, 999; 206/528–540; 700/231, 241
See application file for complete search history.

(56) References Cited

U.S. PATENT DOCUMENTS

| 4,084,695 | A | | 4/1978 | Halbich | |
|---|---|---|---|---|---|
| 4,253,572 | A | | 3/1981 | Halbich | |
| 4,725,999 | A | * | 2/1988 | Tate | ............................ 368/10 |
| 4,793,492 | A | | 12/1988 | Halbich | |
| 5,408,443 | A | * | 4/1995 | Weinberger | ................... 368/10 |
| 5,412,372 | A | | 5/1995 | Parkhurst et al. | |
| 5,646,912 | A | | 7/1997 | Cousin | |
| 5,990,782 | A | | 11/1999 | Lee | |
| 6,048,087 | A | | 4/2000 | Laurent et al. | |
| 6,221,010 | B1 | | 4/2001 | Lucas | |
| 6,259,654 | B1 | | 7/2001 | de la Huerga | |
| 6,294,999 | B1 | | 9/2001 | Yarin et al. | |
| 6,324,123 | B1 | * | 11/2001 | Durso | ......................... 368/10 |
| 6,529,446 | B1 | * | 3/2003 | de la Huerga | ................ 368/10 |
| 6,594,549 | B2 | * | 7/2003 | Siegel | ........................ 700/241 |
| 6,595,365 | B1 | | 7/2003 | Wigmore | |
| 6,625,518 | B2 | * | 9/2003 | Depeursinge | ................ 700/242 |
| 6,626,358 | B1 | * | 9/2003 | Breimesser et al. | ......... 235/380 |
| 6,771,174 | B2 | | 8/2004 | Broas | |
| 6,822,571 | B2 | * | 11/2004 | Conway | .................. 340/573.1 |
| 6,995,675 | B2 | * | 2/2006 | Curkendall et al. | ....... 340/573.3 |
| 2002/0093429 | A1 | * | 7/2002 | Matsushita et al. | ....... 340/573.1 |
| 2003/0043026 | A1 | * | 3/2003 | Noble et al. | ........... 340/309.15 |

(Continued)

OTHER PUBLICATIONS

Website: E-pill, www.epill.com, 2004.

(Continued)

*Primary Examiner*—Benjamin C. Lee
*Assistant Examiner*—Jennifer Mehmood

(57) ABSTRACT

A remote medication delivery system for providing remote monitoring, and optionally delivering, medication to a patient is provided. Specifically, in one embodiment the system comprises at least one dosage containment unit, a sensor for monitoring the status of the unit, and a transmitter for transmitting the status to a remote receiver. A method for remotely monitoring, and optionally delivering, medication to a patient is also provided.

39 Claims, 5 Drawing Sheets

U.S. PATENT DOCUMENTS

2004/0008123 A1* 1/2004 Carrender et al. ..... 340/825.49
2004/0012502 A1* 1/2004 Rasmussen ............ 340/870.16
2007/0093932 A1* 4/2007 Abdulhay et al. .......... 700/231

OTHER PUBLICATIONS

Website: Drugstore.com, www.drugstore.com/products/prod.asp-?pid=55336&catid=32880&aid=336119&aparam=ezy_dose_pill_box_timer_, 2004.

Website: Dynamic Living, www.dynamic-living.com/pill_box.htm, 2004.

Website: Space Savers, spacesavers.com/medpildis.html, 2004.

Website: Nexdose, www.nexdose.com, 2004.

Website: Devine Medical, tore.devinemedical.us/pilcomboxbx6.html, 2004.

Website: Independent Living Aids, www.independentliving.com/products.asp?dept=99&deptname=Pill%20and%20Medicine%20Organizers, 2004.

Website: Safe Home Products, www.safehomeproducts.com/SHP/HH/Pill_Box_Timers.asp.

* cited by examiner

REMOTELY MONITORED MEDICAL SYSTEM

CROSS-REFERENCE TO RELATED APPLICATIONS

This application claims priority to U.S. provisional application No. 60/423,206, filed Oct. 31, 2002, the disclosure of which is incorporated by reference herein.

FIELD OF THE INVENTION

The current invention is directed to remote medication and medical service delivery systems; and more particularly to an apparatus for the monitoring of a patient and/or the delivery of prescribed medications to patients at a remote location.

BACKGROUND OF THE INVENTION

Advances in pharmaceutical technology have led to major improvements in modern healthcare. New pharmaceuticals have been designed to fight bacterial infections, disease, mental disorders, and a variety of other medical conditions. However, many of these pharmaceuticals require very carefully controlled conditions to be effective. For example, although drug "cocktails" or combinations have been very successful in extending the lives and lifestyles of many HIV-positive patients, the drugs often have very complicated protocols. Moreover, failure to follow all of the indications can greatly reduce the efficacy of these drugs.

More problematic still are antibacterial drugs that often have required patients to take the medication for weeks or even months. In these cases, the failure to follow a course of medication to its completion, particularly for bacterial infections, can and does frequently lead to the generation of drug-resistant strains of these bacteria, which in turn require the development of ever more sophisticated drugs.

To address these problems hospitals often turn to in-house dosage routines, which either require a patient to come into the hospital to receive their medication, or require close supervision of the patient throughout the treatment by a healthcare professional. Not only is this practice costly and time-consuming, its success depends on the availability of a large numbers of healthcare professionals. The September 11th terrorist attacks and the anthrax mail attacks on many government agencies around the country, and the subsequent struggles the public health system faced in delivering medication to all the exposed postal personnel, demonstrated the all too real possibility that healthcare disasters either natural or man-made could easily overwhelm the public health system leading to tragic lapses in medication delivery.

The possibility of the public health system being faced with hundreds of thousands, or possible millions, of individuals exposed to either biological or chemical attacks makes it apparent that a system is needed to provide for the remote delivery and monitoring of a patient's medication and overall condition.

SUMMARY OF THE INVENTION

The present invention is directed to a remote medication delivery system for providing remote monitoring, and optionally delivering, medication to a patient.

In one embodiment the system comprises at least one dosage containment unit, a sensor for monitoring the status of the unit, and a transmitter for transmitting the status to a remote receiver. In one such embodiment, the transmitter is activated to send the status automatically when one of the sensors senses that one of the units has been opened. In another such embodiment, each of the dosage units has a unique electronic door identifier such that the identity of the unit being opened is transmitted to the remote receiver along with the status of the unit.

In another embodiment, the system also includes a unique electronic system identifier.

In still another embodiment, the system includes a clock for generating a date and time stamp.

In yet another embodiment, the system includes a global positioning system for determining the geographical position of the system.

In still yet another embodiment, the system includes a data encryption device for encrypting data from the system prior to transmission.

In still yet another embodiment, the transmitter is selected from the group consisting of a two-way pager system, a cellular communication system, and a telemetry RF frequency system.

In still yet another embodiment, the remote receiver is further connected to a database through a network. In such a system the receiver converts the signal from the transmitter into an electronic mail for transmission over the network. In such an embodiment the email may be encrypted prior to transmission and the database may be a secure database.

In still yet another embodiment, the system includes a digital thermometer for recording a patient's temperature.

In still yet another embodiment, the system includes at least one memory device for storing data generated by the system prior to transmission.

In still yet another embodiment, the system includes a data entry device for entering data into the system. In one such embodiment the data entry device is an alphanumeric keypad. The data entered in such an embodiment may include preset codes indicative of a patient's condition. In such an embodiment, the remote receiver may also include a programmable controller for analyzing data entered into the system for a patient's condition and communicating the patient's condition to a user, such as medical personnel. In such an embodiment, the data transmission means may include electronic mail, a page, or a hardwired monitor and may be integrated with or independent from the receiver.

In still yet another embodiment, the system includes a digital scale for recording a patient's weight.

In still yet another embodiment, the system includes a digital blood pressure monitor for recording a patient's blood pressure.

In still yet another embodiment, the system includes a mechanical interlock system to prevent the non-sequential opening of the dosage containment units. In such an embodiment, the interlock system may include a timer such that each lock is unlocked automatically when it is time for a patient to take a medication.

In still yet another embodiment, the system includes a programmable timer for storing one or more medication dosage schedules having any number of medication events therein. In such an embodiment, the system may be designed to automatically transmit the status of the units at a predetermined time interval. The system may also include an alarm to provide an indication to a patient of the appropriate time for taking a medication. The alarm may also or independently include a remote patient notification system to communicate the medication time to a patient remotely. This remote communication system may include any suitable device including a pager, a cellular phone, a telemetry RF frequency, etc.

In another embodiment, the invention is also drawn to a method of remotely controlling the medication of a patient, using a system as described above.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
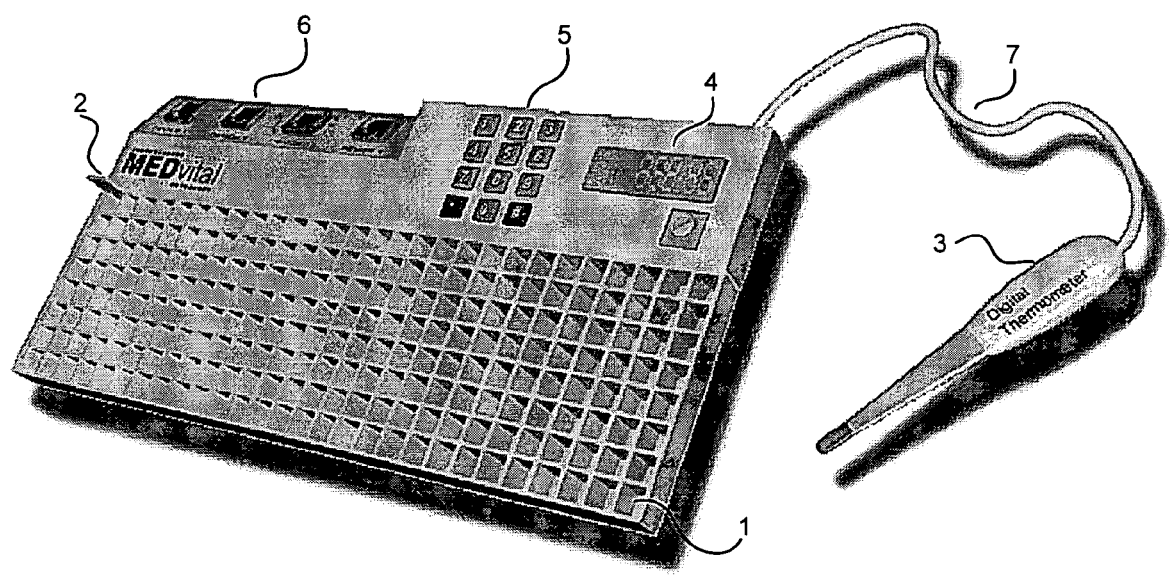
FIG. 1 is a somewhat schematic diagram of one embodiment of a remotely monitored medical system in accordance with the invention.

The current invention is directed to a remotely monitored medical system, or RMMS. One exemplary embodiment of an RMMS is that of a "smart pillbox" as shown in FIG. 1. In this embodiment, the RMMS is a pillbox preloaded with a medication regimen. As shown in FIG. 1, each RMMS contains at least one medication matrix comprised of multiple dosage containment units (DCUs) 1. Each DCU 1 is designed as an individual containment and dispensing unit for a predetermined dosage of the contained medication(s), and each DCU is arranged with at least one door 2 such that the contained medication(s) are retained within the DCU until the DCU is opened and the medication consumed by the patient. Although not required, to ensure the safety of the patient, each DCU may be preloaded and then hermetically and sterilely sealed with a visible tamper proof seal (not shown).

Figure 2:
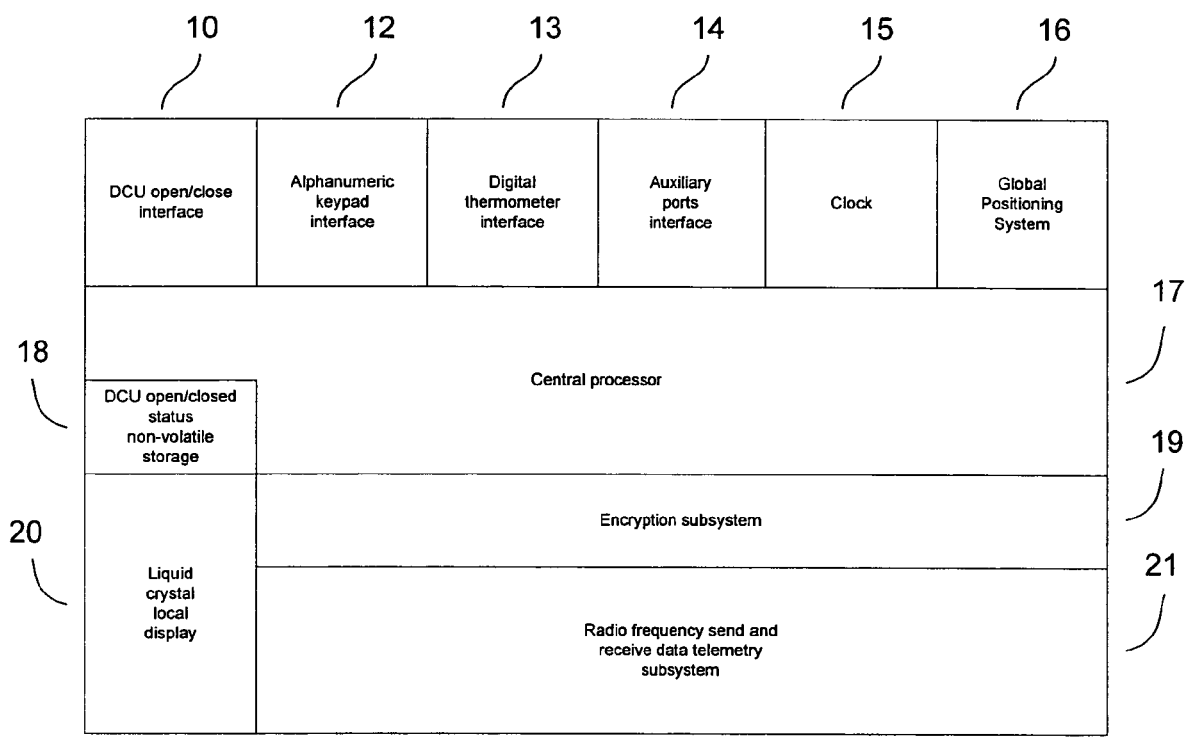
FIG. 2 is a block diagram of one embodiment of a remotely monitored medical system in accordance with the invention.

As shown schematically in FIG. 2, each of the DCUs is also connected to a door sensor or interface 10 which monitors the open/close status of a door. During operation, once a door is opened (as shown in FIG. 1) the door monitor sensor switches the status indicator from the closed to the opened position. Although the doors 2, as shown in FIG. 1, may be indistinguishable from each other, and therefore may also be opened in any order desired, in a preferred embodiment each DCU is clearly labeled on its face with a number that corresponds to the order in which it should be opened. In addition, each door may also have a unique electronic address that corresponds to its physical position in the numerical opening sequence, i.e., the door to the fifth DCU to be opened would be printed on its face with the number 5, and would have an electronic address of 5, such that upon opening the door the electronic address would record its status uniquely, such as, for example, in a bit location in a non-volatile Open/Closed status array 18, as depicted in the box diagram in FIG. 2. In such an embodiment, once a DCU is opened its corresponding Open/Close bit is permanently set to an Open status.

In addition to the sensor and status indicator 10 described above, the doors 2 of the DCUs 1 may also be interlocked by a mechanical means such as opening tabs for each DCU that are not revealed until the preceding DCU has been opened, such that each DCU must be opened in numerical sequence beginning with the first DCU and following in ascending order. Such sequentially controlled opening permits variable dosing to accommodate medication loading requirements and/or additional medication regimens within the primary medication regimen.

The RMMS of the current invention is also designed to be remotely monitored and/or operated. Accordingly, each RMMS is also provided with a transmitter 6 such that the status of each DCU 1 may be transmitted to a remote receiver (not shown) and thereby the status of the RMMS and each DCU remotely monitored. Although as shown in FIG. 1 the transmitter 6 may comprise a hardwired interface such as through a modem connection to an external data or telephone line, the RMMS may also comprise a wireless transmitter, such as, for example, a two-way pager system, a cellular system, a suitable RF radio frequency, or any other suitable data transmission system, such as over the Internet via an email or web-broadcast system. In addition to the actual transmitter, the data generated for transmission by an RMMS unit of the current invention can be in any suitable format. For example, in one embodiment the RMMS unit places the data into an email message format, adds the appropriate email headers (such as for SMTP for example), and transmits the email. The message can also alternatively be encrypted and error checked if desired prior to transmission. Regardless of the transmission system used and the format of the data transmission itself, it should be understood that the RMMS unit of the current invention is in communication with a remote receiver such that the desired medical personnel can adequately monitor the medication and/or medical condition of the patient user.

The transmitter 6 may be triggered by any suitable means. For example, in one embodiment the transmitter may be activated manually by the user after each dosage of medication is taken, however, in a preferred embodiment the opening of the door on a DCU, and the setting of its status bit to Open by the DCU sensor/interface automatically triggers the transmitter to transmit an RMMS status update. In such an embodiment, as shown in FIG. 2, the RMMS Open/Closed status data array 10 is scanned, and optionally stored in a memory device 18, such as a non-volatile memory device, then the result of the scan is formatted, and converted into transmittable packets by the data system central processor 17 that then activates a transmitter 21 to send a signal to a central database (not shown). Accordingly, in such an embodiment, each time one of the several DCUs 1, is opened to take the medication contained therein the status of the door is monitored, recorded, and transmitted to a remote monitor.

Although, the above description provides the basic system necessary for the operation of the RMMS in accordance with the current invention, it should be understood that the RMMS may include a number of peripheral medical monitoring devices, and subsystems to enhance the capabilities of the system.

For example, in one embodiment the RMMS unit may include a unique electronic identifier such that when the RMMS unit broadcasts its status to the remote receiver it also broadcasts a unique identification code such that the remote monitor can be sure of the identity of the broadcasting unit.

The RMMS unit may also include a clock and/or calendar 15, as shown in FIG. 2, to provide date and time data. In such an embodiment the clock may be interconnected with a central processor 17 and/or the DCU door sensor/interface 10 such that when a door 2 is opened and a status update is sent, a date and time stamp may also be applied to the data. In one embodiment, the clock may also contain a timer and a programmable timer memory such that a medication dosage schedule may be programmed into the RMMS unit. Such a timer may in turn be connected to an alarm system to provide an indication to the user that the time for taking a medication dosage is due. Such an alarm system may take any suitable form, such as for example, an audible alarm or a visual indicator such as an alarm light. Alternatively, the alarm system may include a remote indication system, such as a two-way pager system or any other RF radio broadcasting system such that the alarm may be transmitted to a user's attention remotely on a standard pager, cellular telephone, or other receiver. In such an RMMS unit the timer may also be interconnected with the mechanical interlock system such that each door 2 is only unlocked and may thus only be opened at a time determined by the medication schedule programmed therein. It should be further understood that although the timer may be designed such that the user can program and reprogram the timer and clock system manually, the RMMS unit and timer may also be designed such that it is preprogrammed prior to issuance to a user, and/or may be interlinked with the transmitter and central processor such that medical personnel can remotely program and reprogram the timer through the data link.

In addition to an onboard clock/timer, an RMMS unit in accordance with the current invention may also include a global positioning system 16 (GPS), as shown in FIG. 2, such that the geographical location of the RMMS unit may be determined. In such an embodiment the global positioning system may be interconnected to a memory device through a central processor such that the geographical location of the RMMS unit can be stored into memory and transmitted by the transmitter to the remote receiver. In one preferred embodiment the global positioning system 16 is automatically activated to obtain the geographical location data of the RMMS unit upon activation of a data transmission event. In such an embodiment, once a DCU door 2 is opened and the door status sent to the transmitter for transmission to the remote sensor, the global positioning system is also activated, the geographical location data taken and combined with the door status data and transmitted to the remote receiver such that the location of the patient can be determined by the monitoring medical personnel.

In yet another embodiment, the RMMS unit may also include one or more peripheral vital monitors. For example, in one embodiment, as shown in FIG. 1, the RMMS unit may include a digital thermometer 3, which may be attached to the RMMS base unit via a data cable tether 7, and may also dock into a slot (not shown) in the RMMS unit for storage. Such a thermometer may be used to record a patient's temperature when required. The RMMS unit may also include a digital scale (not shown) with local display attached via an appropriate data tether to the RMMS unit, or alternatively a digital auto-inflating blood pressure monitor with local display attached through an appropriate data tether to the RMMS unit, such as through an auxiliary data port 6 (as shown in FIG. 1) and 14 (as shown in FIG. 2). As it should be understood, other digital health or fitness monitors may also be included as required. In any such embodiment, the optional vital monitors may be interfaced directly to the RMMS unit data system, such as the central processor 17 and/or memory 18 such that the data may be recorded and transferred for immediate storage into a temporary memory. In an embodiment of the RMMS unit, the transfer and storage of the peripheral measurement data automatically triggers the data system to transmit the status of the RMMS unit and the auxiliary data to the remote receiver.

As shown in FIG. 1, the RMMS unit may also include a data entry device, such as an alphanumeric keypad, such as a the type found on a telephone 5, that the individual can use to enter and transmit other data to the remote receiver. For example, the data transmitted may include predetermined codes that correspond to developing symptoms, such as dizziness, blurry vision, uncontrolled bleeding, etc (ex. A1 for dizziness, A2 for blurry sight, B1 for body tremors, etc.). In such an embodiment, the data may either be manually transferred by user action, or the central processor may be adapted to enter the data automatically into memory and transmit the data to the remote receiver along with the rest of the RMMS unit status data. In such an embodiment, the RMMS unit may be designed to automatically review the transmitted data, for example, by a database program that scans all the database records for "out-of-bounds" conditions, such as combinations of symptoms that may indicate that the patient is in a medically dangerous condition, and if such an "out-of-bound" alert is detected the RMMS unit may be designed to automatically transmit the data to the remote receiver. Alternatively, the receiver may be designed to contain and execute such a database program. Regardless of whether the transmitter or receiver monitors the codes for dangerous conditions, multiple levels of medical alerts can then be established by programming the automatic database processes to automatically notify the supervising medical personnel of individuals that need further review. The alerts can be sent to the supervising medical personnel by any suitable method, such as by email, two-way pager, cellular phone transmission, or alert screens on their monitors. Although the above discussion assumes that the data entry device 5 is integrated with the RMMS unit, such a device may also be a peripheral that is connected through a data tether into one of the auxiliary ports 6.

In addition, to the above data entry devices the RMMS unit may also include a data display device 4, as shown in FIG. 1. In such an embodiment the display device may comprise any suitable system for communicating information to a user, such as an LED display or a liquid crystal display. As shown in FIG. 2, the display device 20 may be directly interconnected with the other data entry and monitoring devices of the RMMS unit, such as through the central processing unit 17 such that any information entered from any of the peripheral devices, such as the digital thermometer 14, the clock 15, or the data entry device 13 may be displayed on the display device. Like any of the other peripheral devices, the display device described above may also be interconnected with the RMMS unit through a data tether into an auxiliary port interface 14.

In addition to the various peripheral devices discussed above, an RMMS unit in accordance with the current invention may also include an encryption system 19, as shown in FIG. 2 interconnected with the transmission system 21 such that data transmitted from the RMMS unit is securely encrypted to protect the data during broadcast. In such an embodiment a suitable encryption system may be utilized with the current invention such that data may be encrypted and transmitted to the remote receiver.

Although the above-discussion has focused on an RMMS base unit having a pill distribution function, the current invention is also generally directed to a remote medical monitoring system. For example, an RMMS unit might comprise a base unit only designed to provide a selection of medical monitoring devices and other data entry systems. Specifically, in one embodiment for diabetics the RMMS unit might comprise an electronic scale device, a blood pressure monitoring peripheral, and a glucose tester such that all relevant medical information can be entered into the system and transmitted to remote medical personnel for analysis. It should be understood that any suitable combination of medical testing devices may be combined through peripheral electronic devices into a data collection/transmission RMMS unit as described above such that the condition of a patient can be remotely monitored by medical personnel.

Regardless of the specific combination of medical analysis or medication dispensing devices connected to the RMMS unit according to the current invention, the data transmission once triggered are transmitted from the RMMS unit by a suitable transmission device, such as a radio frequency connection like a 2-way pager telemetry signal, to a receiver that retransmits the data, such as by converting it into an Internet email, and sends it to a secure database at a central medical monitoring facility. For example, in an RMMS unit including a plurality of DCUs, an electronic RMMS signature, a thermometer, other optional peripheral devices, and a GPS system, the data transmission packets are constructed to include a unique RMMS kit identifier number, the Open/Close status condition of the DCUs in the kit, the data reading from the thermometer if appropriate, the data reading from any optional vital monitors that are in use with the system, the GPS position of the unit, a public key if appropriate, the email address of the central medical monitor database, and an error-checking construct such as a CRC field. The data transmission thus constructed is then sent to the remote receiver where they are converted into Internet email (SMTP) messages and transmitted to the central medical monitor database.

Figure 3:
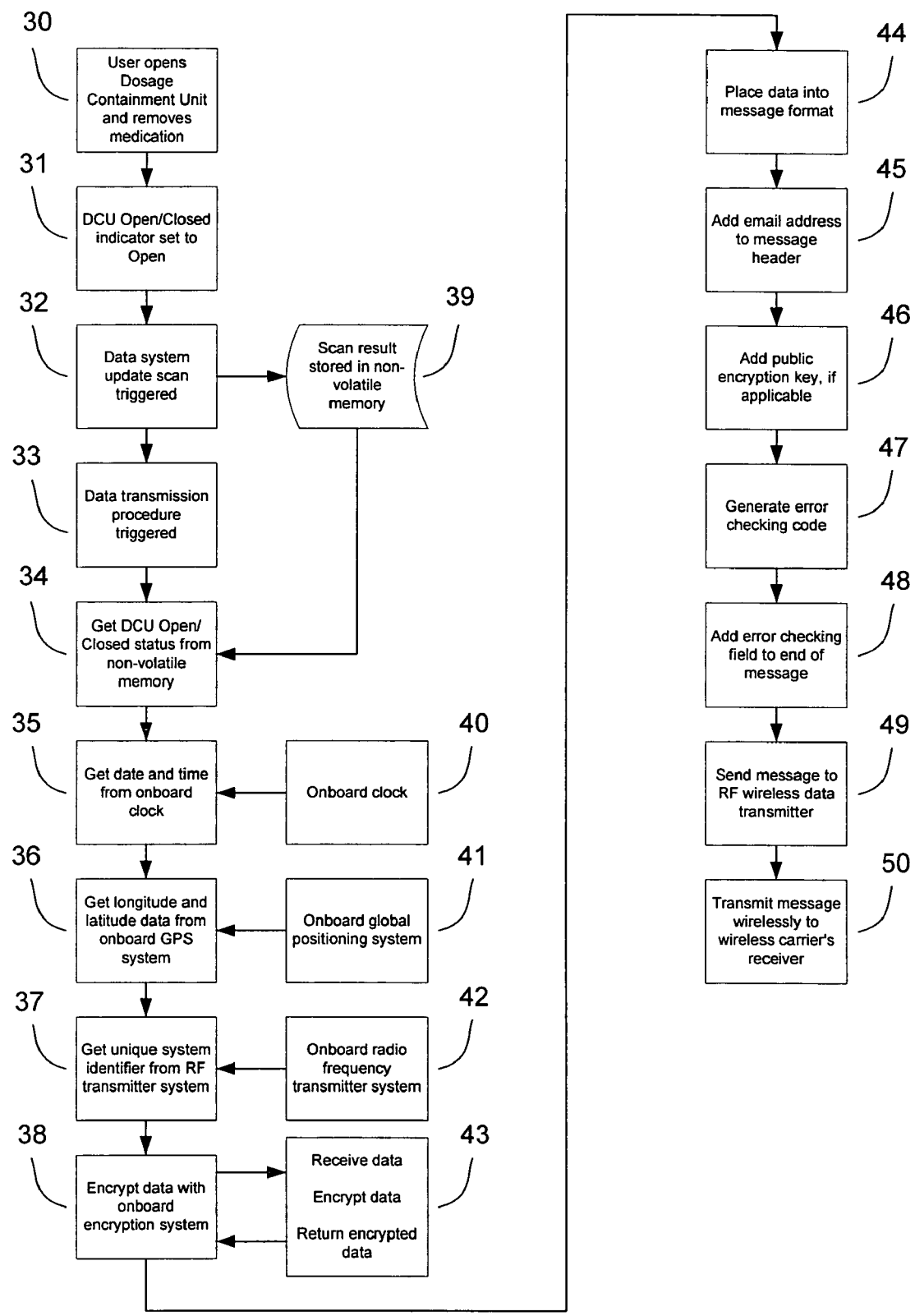
FIG. 3 is a flowchart of the operation of one embodiment of the data collection and transmission functions of a remotely monitored medical system in accordance with the invention.
Figure 4:
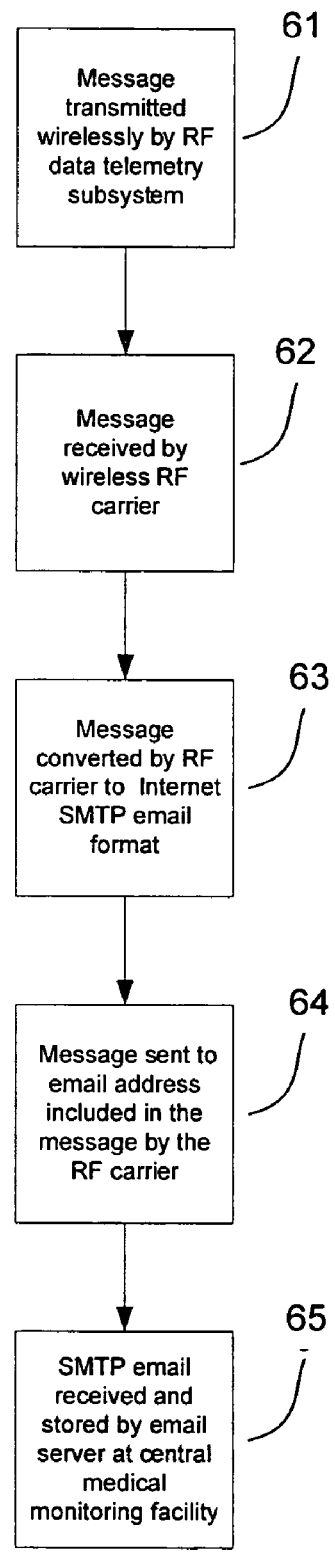
FIG. 4 is a flowchart of the operation of one embodiment of the reception functions of a remotely monitored medical system in accordance with the invention.
Figure 5:
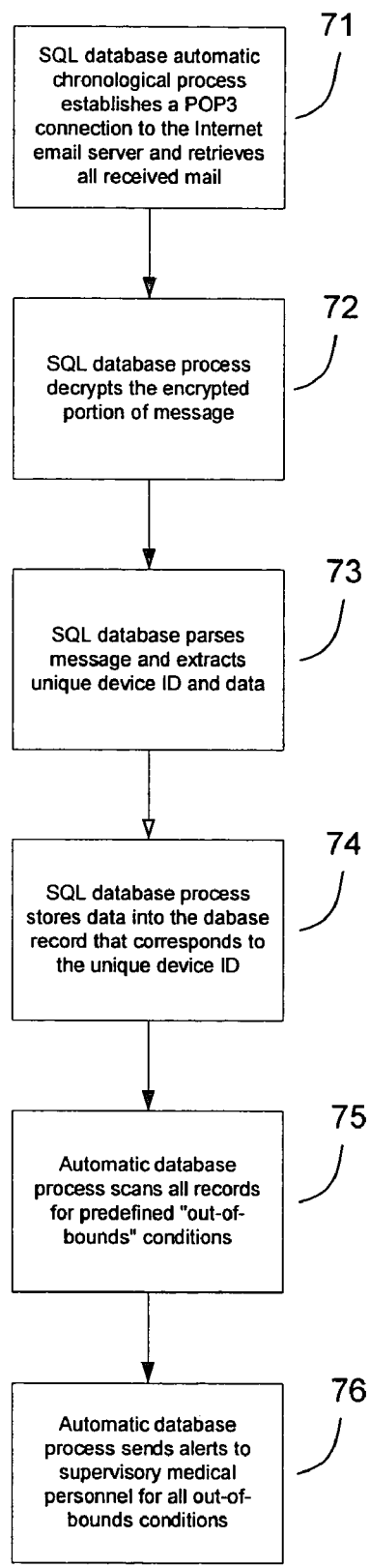
FIG. 5 is a flowchart of the operation of one embodiment of the database functions of a remotely monitored medical system in accordance with the invention.

FIGS. 3 to 5 all show flowcharts of the operation of an RMMS unit in accordance with an embodiment of the current invention having a plurality of DCUs. As shown in FIG. 3, during operation, once a dosage containment unit is opened 30 and its corresponding Open/Close bit set to "open" 31 a series of data updating and transmission procedures are triggered. First, the detection of an opening of a DCU by the DCU door sensor, and the setting of the DCUs status bit to "open", triggers an RMMS status update by the data system 32. In one embodiment, the RMMS Open/Closed status data array is scanned and stored in non-volatile memory 39. Alternatively, a data transmission procedure may be immediately and automatically triggered by the DCU opening 33. Regardless of whether the data is initially stored for later retrieval 34 and transmission at either a manual, or timed transmission trigger, or immediately and automatically transmitted upon opening of the DCU, once the transmission procedure is triggered, the result of the scan is then formatted, and converted into transmittable packets by the data system central processor.

If the RMMS unit has additional peripheral devices, such as an onboard clock 40, an onboard GPS 41, a unique electronic identifier 42, and/or encryption system 43, as shown in FIG. 3, then once a transmission procedure is triggered, each of these devices is queried by the system. For example, if the RMMS unit contains a clock chip 40, the system queries the clock, which provides the data system with the current date and time 35. Likewise, if the RMMS unit contains a Geographic Positioning System (GPS) 41 that determines the physical location of the RMMS unit, the system queries the GPS which provides the relevant geographical data to the data system 36.

Although not shown in FIG. 3, if the RMMS unit has other peripheral monitoring systems, such as a digital thermometer, a digital scale, a digital auto-inflating blood pressure monitor, or other digital health or fitness monitors or data input devices such as an alphanumeric keypad that may be employed by the user to enter predetermined symptom codes (ex. A1 for dizziness, A2 for blurry sight, B1 for body tremors), the optional vital monitors interface directly to the Medication System's data system. During operation, they capture the measurement data, and transfer it to the Medication System's data system for immediate storage into temporary memory. The data may then wait for the activation of a data transmission procedure, such as when a DCU is opened, or during a scheduled transmission event, or the transfer and storage of the measurement data may itself trigger the data system to enter into a data transmission sequence.

Once all of the data is retrieved it may either be directly prepared for transmission, or where available a unique RMMS unit identifier can be retrieved 37 from an onboard RMMS electronic identifier system 42 and then the combined data sent to an encryption system 38 prior to transmission. The encryption system in turn encrypts at least a portion of the data and then returns the encrypted data to the transmission procedure 43.

Regardless, of what peripherals are attached to the RMMS and what encryption and identification devices are utilized, once the RMMS data system retrieves the data from the temporary storage area and validates and normalizes the data. Then the data is formatted into data transmission packets, 44-45, the public encryption key 46 and error-checking construct and code 47-48 are added to the data transmission packets, and the data packets are sent to a transmitter 49 and transmitted via a radio frequency transmitter to the central RMMS remote monitor database 50.

The data transmission is designed to contain all relevant data generate by the RMMS unit. For example, in the embodiment described above, the data transmission packets are constructed to include a unique RMMS kit identifier number, the Open/Close status condition of the DCUs in the kit, the data reading from the thermometer if appropriate, the data reading from any optional vital monitors that are in use with the system, the GPS position of the unit, a public key if appropriate, the email address of the central medical monitor database, and an error-checking construct such as a CRC field.

As shown in FIG. 4, in one embodiment once data packets are transmitted 61 via the radio frequency transmitter to the radio frequency supplier's ground station 62 they are converted into Internet email (SMTP) messages 63 and transmitted to the central medical monitor database 64-65. It should be understood that although the above embodiment only discusses the transmission of the message to the database via the Internet that any suitable means of transmitting the data received by the receiver to a secure database may be employed by the current invention. For example, the remote receiver could itself contain a transmitter capable of transmitting data wirelessly to the database, or alternatively the database itself might include the receiver such that no further transmission of the data is required.

Regardless of the means of transmitting the data from the receiver to the database, as shown in FIG. 5, once the data packets arrive at the secure RMMS remote monitor central database they are read 71, decrypted if necessary 72, and the data parsed 73 and placed into the database file that corresponds to the RMMS kit unique identifier number 74. During this process the data may be date and time stamped upon its placement into the database. Although not necessary, in the embodiment shown in FIG. 5, the placement of the data into the database file may further trigger an immediate medical profile update 75. In such a medical profile update the database scans the patient's records for "out-of-bounds" or potentially dangerous medical indications and predetermined statistical and alarm procedures are applied to the medical profile. If any alarm conditions are found to exist predefined notification procedures are then implemented 76. The notification procedures will be established to correspond to the severity of the alarm condition generated by the deviation in the medical profile. For example, the range of notifications could be from a simple entry into a periodic report table to immediate notification of standby medical personnel. Such notification could then be delivered to the medical personnel by any suitable means, such as two-way paging, cellular phone communication, or via email through the Internet. Regardless of the method of the alert, it should be understood that the database of the RMMS system in accordance with the current invention may include a remote access feature such that after correct authorization and authentication all medical profiles can be accessed via simple web browsers operating in a secure mode As described above, the exact combination of monitoring devices and medications placed into the RMMS unit, such a system provides the capability to monitor great numbers of patients in an efficient manner. For example, the data handling requirements of even a million units in operation is trivial for current database operations. Thusly an enormous number of individuals can be medicated and monitored and those that develop serious symptoms can be identified and admitted into the existing public health hospitalization and treatment facilities.

Accordingly, although specific embodiments are disclosed herein, it is expected that persons skilled in the art can and will design alternative remote medical monitoring systems and methods of remotely monitoring the medical condition of a patient that are within the scope of the following claims either literally or under the Doctrine of Equivalents.

What is claimed is:

1. A remotely monitored medication delivery system comprising: at least one dosage containment unit defining an internal volume, each of the at least one containment units having at least one moveable door defining an opening thereto; a sensor in signal communication with each of the at least one moveable door for monitoring the status of said door and producing a signal indicative of said status: and a transmitter in signal communication with said sensor for receiving the signal from said sensor and transmitting the signal to a remote receiver, further comprising a data entry device in at least indirect signal communication with said transmitter such that data entered into said remotely monitored medication delivery system is transmitted to said remote receiver by said transmitter, further comprising a data entry device in at least indirect signal communication with said transmitter such that data entered into said remotely monitored medication delivery system is transmitted to said remote receiver by said transmitter wherein the remote receiver further comprises: a programmable controller having a predefined alert table programmed therein in at least indirect signal communication with said remote receiver, wherein said alert table contains alert codes for each of at least one or more predetermined codes; and a second transmitter in at least indirect signal communication with said programmable controller, wherein said programmable controller receives said data from said remote receiver, scans said data for the at least one or more predetermined codes, compares said at least one predetermined code versus said alert table, and generates at least one alert code based on said alert table, and wherein said second transmitter is activated to send said data to at least one supervising medical attendant when indicated by said alert code.

2. The remotely monitored medication delivery system described in claim 1, wherein said transmitter is activated to send the signal automatically when one of said sensors senses that one of the at least one of said doors has been opened.

3. The remotely monitored medication delivery system described in claim 1, further comprising a unique electronic system identifier, wherein said unique electronic system identifier is transmitted to the remote receiver along with the status of said at least one door.

4. The remotely monitored medication delivery system described in claim 1, further comprising a clock apparatus in at least indirect signal communication with said transmitter for generating a date and time stamp, wherein said date and time stamp is transmitted to the remote receiver along with the status of said at least one door.

5. The remotely monitored medication delivery system described in claim 1, further comprising a global positioning system in at least indirect signal communication with said transmitter for determining the geographical position of said system, wherein said position is transmitted to the remote receiver along with the status of said at least one door.

6. The remotely monitored medication delivery system described in claim 1, further comprising a data encryption device in at least indirect signal communication with said transmitter, wherein any transmission is received and encrypted by said data encryption device prior to transmission by said transmitter.

7. The remotely monitored medication delivery system described in claim 1, wherein each of said at least one of said doors includes a unique electronic door identifier such that the unique electronic door identifier is transmitted to the remote receiver along with the status of said at least one door.

8. The remotely monitored medication delivery system described in claim 1, wherein the transmitter is a two-way pager telemetry system.

9. The remotely monitored medication delivery system described in claim 1, wherein the remote receiver is further connected to a database through a network, such that when said receiver receives a signal from the transmitter, the receiver converts said signal to an electronic mail and transmits said electronic mail to said database through said network.

10. The remotely monitored medication delivery system described in claim 9, wherein said receiver further comprises an encryption system such that said electronic mail is encrypted prior to transmission.

11. The remotely monitored medication delivery system described in claim 9, wherein said database is a secure database.

12. The remotely monitored medication delivery system described in claim 1, further comprising a digital thermometer in at least indirect signal communication with said transmitter for recording a patient's temperature said transmitter further configured to communicate said temperature to the remote receiver.

13. The remotely monitored medication delivery system described in claim 12, further comprising a memory device for at least temporarily storing said temperature prior to transmission.

14. The remotely monitored medication delivery system described in claim 1, wherein the data entry device is an alphanumeric keypad.

15. The remotely monitored medication delivery system described in claim 1, wherein the at least one predetermined code corresponds to a specific patient symptom.

16. The remotely monitored medication delivery system described in claim 1, wherein said second transmitter transmits said data through a medium selected from the group consisting of electronic mail, a page, or a hardwired monitor.

17. The remotely monitored medication delivery system described in claim 1, further comprising at least one internal memory device for at least temporarily storing data generated by said system at least one of either prior to or after transmission by said transmitter.

18. The remotely monitored medication delivery system described in claim 1, further comprising at least one internal memory device for at least temporarily storing signals generated by said system at least one of either prior to or after transmission by said transmitter.

19. The remotely monitored medication delivery system described in claim 1, wherein the system comprises a plurality of dosage containment units.

20. The remotely monitored medication delivery system described in claim 19, wherein said plurality of units are arranged in a sequential order such that each of the plurality of doors except a first door and a last door has one preceding door and one succeeding door, and wherein said system further comprises a mechanical interlock system engaged with said plurality of doors such that the interlock system locks each succeeding door until the door immediately preceding said succeeding door is opened.

21. The remotely monitored medication delivery system described in claim 1, further comprising a digital scale for recording a patient's weight in at least indirect signal communication with said transmitter, said transmitter further configured to communicate that weight to the remote receiver.

22. The remotely monitored medication delivery system described in claim 1, further comprising a digital blood pressure monitor for recording a patient's blood pressure in at least indirect signal communication with said transmitter, said transmitter further configured to communicate that blood pressure to the remote receiver.

23. The remotely monitored medication delivery system described in claim 1, wherein the system transmitter is designed to automatically transmit the signals indicative of the status of the at least one door at a predetermined time interval.

24. The remotely monitored medication delivery system described in claim 1, further comprising a programmable timer, wherein the timer may be programmed with at least one medication dosage schedule having at least one medication event.

25. The remotely monitored medication delivery system described in claim 24, further comprising an alarm in signal communication with said programmable timer such that when the at least one medication schedule indicates a medication event the alarm is activated to provide an indication to a patient.

26. The remotely monitored medication delivery system described in claim 24, further comprising a remote patient notification system in signal communication with said programmable timer such that when the at least one medication schedule indicates a medication event the remote patient notification system is activated to communicate the event to a patient remotely.

27. The remotely monitored medication delivery system described in claim 26, wherein the remote patient notification system comprises a communication system selected from the group consisting of a pager, a cellular phone, and a telemetry RF frequency.

28. The remotely monitored medication delivery system described in claim 24, further comprising at least one locked mounted on each of said at least one doors, wherein each said at least one lock is in signal communication with said programmable timer such that each said at least one lock is unlocked automatically when said programmable timer indicates the occurrence of a medication event.

29. A remotely monitored medication delivery system comprising: a plurality of dosage containment units, each unit defining an internal volume and having at least one moveable door defining an opening thereto, wherein said plurality of units are arranged in a sequential order such that each of the plurality of doors except a first door and a last door has one preceding door and one succeeding door, a mechanical interlock system engaged with said plurality of doors such that the interlock system locks each succeeding door until the door immediately preceding said succeeding door is opened; a sensor in signal communication with the at least one moveable door for monitoring the status of said door and producing a signal indicative of said status, wherein each of said plurality of doors includes a unique electronic door identifier such that the unique electronic door identifier is transmitted to the transmitter along with the signal; a transmitter in signal communication with said sensor for receiving the signal from said sensor and transmitting the signal to a remote receiver, wherein said transmitter is activated to send the signal automatically when said sensor senses that one of the plurality of doors has been opened; an electronic system identifier uniquely indicative of the particular remotely monitored medical system, wherein said electronic system identifier is transmitted to the remote receiver along with the signal; a clock apparatus in at least indirect signal communication with said sensor and said transmitter, wherein the date and time is generated by the clock and transmitted to the transmitter for transmission to the remote receiver when the sensor indicates that one of the plurality of doors has been opened; a data entry device in at least indirect signal communication with said transmitter such that data entered into said remotely monitored medication delivery system is transmitted to said remote receiver by said transmitter; and an encryption device in at least indirect signal communication with said transmitter, wherein any transmission is received and encrypted by said data encryption device prior to transmission by said transmitter.

30. The remotely monitored medication delivery system described in claim 29, wherein the data entry device is an alphanumeric keypad.

31. The remotely monitored medication delivery system described in claim 29, wherein the data includes at least one predetermined code indicative of a patient's condition.

32. The remotely monitored medication delivery system described in claim 31, wherein the at least one predetermined code corresponds to a specific patient symptom.

33. The remotely monitored medication delivery system described in claim 31, wherein the remote receiver further comprises: a programmable controller having a predefined alert table programmed therein in at least indirect signal communication with said remote receiver, wherein said alert table contains alert codes for each of at least one or more predetermined codes; and a second transmitter in at least indirect signal communication with said programmable controller, wherein said programmable controller receives said data from said remote receiver, scans said data for the at least one or more predetermined codes, compares said at least one predetermined code versus said alert table, and generates at least one alert code based on said alert table, and wherein said second transmitter is activated to send said data to at least one supervising medical attendant when indicated by said alert code.

34. The remotely monitored medication delivery system described in claim 33, wherein said second transmitter transmits said data through a medium selected from the group consisting of electronic mail, a page, or a hardwired monitor.

35. The remotely monitored medication delivery system described in claim 29, further comprising a digital thermometer for recording a patient's temperature in at least indirect signal communication with said transmitter, said transmitter further configured to communicate that temperature to the remote receiver.

36. The remotely monitored medication delivery system described in claim 29, further comprising a memory device for at least temporarily storing said temperature prior to transmission.

37. The remotely monitored medication delivery system described in claim 29, further comprising at least one internal memory device for at least temporarily storing data generated by said system at least one of either prior to or after transmission by said transmitter.

38. The remotely monitored medication delivery system described in claim 29, further comprising a digital scale for recording a patient's weight in at least indirect signal communication with said transmitter, said transmitter further configured to communicate that weight to the remote receiver.

39. A method for remotely delivering medication comprising: providing to a patient the remotely monitored medication system of claim 1; filling each of said at least one dosage containment units with at least one medication dosage; and monitoring said remote receiver to determine the patient's compliance with a medication schedule.

* * * * *